United States Patent
Georgiou et al.

(10) Patent No.: US 9,656,020 B2
(45) Date of Patent: May 23, 2017

(54) GLUCAGON PUMP CONTROLLER

(75) Inventors: Pantelis Georgiou, Wembley Middlesex (GB); Kok Thay Lim, Kuala Lumpur (MY); Christofer Toumazou, London (GB)

(73) Assignee: IMPERIAL INNOVATIONS LIMITED, London (GB)

( * ) Notice: Subject to any disclaimer, the term of this patent is extended or adjusted under 35 U.S.C. 154(b) by 1200 days.

(21) Appl. No.: 13/377,358

(22) PCT Filed: Jun. 9, 2010

(86) PCT No.: PCT/EP2010/058101
§ 371 (c)(1),
(2), (4) Date: May 30, 2012

(87) PCT Pub. No.: WO2010/142734
PCT Pub. Date: Dec. 16, 2010

(65) Prior Publication Data
US 2012/0232519 A1 Sep. 13, 2012

(30) Foreign Application Priority Data
Jun. 10, 2009 (GB) .................................. 0909948.2

(51) Int. Cl.
*A61M 5/168* (2006.01)
*A61M 5/172* (2006.01)
(Continued)

(52) U.S. Cl.
CPC ....... *A61M 5/1723* (2013.01); *G06F 19/3468* (2013.01); *A61M 2005/14208* (2013.01)

(58) Field of Classification Search
CPC .................. A61M 5/1723; A61M 2005/14208
See application file for complete search history.

(56) References Cited

U.S. PATENT DOCUMENTS

| 3,837,339 A | 9/1974 | Aisenberg et al. |
| 5,049,141 A | 9/1991 | Olive |

(Continued)

FOREIGN PATENT DOCUMENTS

WO 2007049961 A2 5/2007

OTHER PUBLICATIONS

Grant, Matthew, Quick Start for Beginners to Drive a Stepper Motor, Freescale Semiconductor, Rev. 1, Jun. 2005, pp. 1, 5.*
(Continued)

*Primary Examiner* — Laura Bouchelle
(74) *Attorney, Agent, or Firm* — Kaplan Breyer Schwarz & Ottesen, LLP (57) ABSTRACT

According to a first aspect of the present invention there is provided a controller for controlling a glucagon pump. The controller comprises an input 8 for receiving an input signal indicative of a measured blood glucose concentration, an output 9 for providing a pulsed glucagon pump drive signal, each pulse being arranged to cause a glucagon pump to deliver a volume of glucagon, and a processing unit 10 for setting the pulse frequency of the pump drive signal in dependence upon the input signal, such that when the input signal indicates that the measured blood glucose concentration is above a threshold concentration the pulse frequency is zero and when the input signal indicates that the measured blood glucose concentration is below the threshold concentration the pulse frequency is increased as the measured blood glucose concentration decreases.

6 Claims, 6 Drawing Sheets

(51) Int. Cl.
*G06F 19/00* (2011.01)
*A61M 5/142* (2006.01)

(56) References Cited

U.S. PATENT DOCUMENTS

| | | | |
|---|---|---|---|
| 5,474,552 A | 12/1995 | Palti | |
| 5,800,420 A * | 9/1998 | Gross et al. | 604/890.1 |
| 6,572,545 B2 * | 6/2003 | Knobbe et al. | 600/365 |
| 2005/0137522 A1 | 6/2005 | Aoki | |
| 2006/0122098 A1 | 6/2006 | Aoki | |
| 2006/0276771 A1 | 12/2006 | Galley et al. | |
| 2007/0088271 A1 * | 4/2007 | Richards | 604/151 |

OTHER PUBLICATIONS

Internet Citation, "Biological neuron model", Mar. 7, 2010, Page(s) Paragraph 02.1, Publisher: URL:http://en.wikipedia.org/wiki/Biological_neuron_model, XP007913982, Published in: Retrieved from the Internet.

Ratchada Pattaranit and Hugo Antonius Van Den Berg, "Mathematical models of energy homeostasis", "ISSN: 1742-5689, XP007913985", Jul. 8, 2008, pp. 119-1135, vol. 5, No. 8, Publisher: Journal of the Royal Society, Interface.

Intellectual Property Office, "British Search Report for International Application No. GB0909948.2", Oct. 5, 2009, Publisher: IPO, Published in: GB.

"International Search Report for Intl Application No. PCT/EP2010/058101", Jul. 28, 2010, Publisher: EPO Published in: NL.

* cited by examiner

GLUCAGON PUMP CONTROLLER

TECHNICAL FIELD

The present invention relates to a controller for controlling a glucagon pump, and a system for controlling blood glucose concentration making use of a controller for controlling a glucagon pump.

BACKGROUND

The pancreas is a glandular organ situated behind the lower stomach. Its main roles in the body include blood glucose homeostasis and the production of digestive enzymes to break down the food we eat. The pancreas produces and releases substances directly into the bloodstream (endocrine functions) and through ducts (exocrine function). The endocrine tissue of the pancreas is made up of clusters of cells called the Islets of Langherans which are responsible for producing the hormones necessary to control blood glucose. The predominant cells which make up each Islet include alpha cells, beta cells and delta cells. The beta cells are responsible for producing and secreting insulin (by the process of exocytosis) when blood glucose levels are high. Insulin acts to cause glucose uptake into surrounding muscle and adipose tissue and triggers the synthesis of fatty acids and glycogen in the liver, which reduces blood glucose and prevents prolonged hyperglycaemia. The alpha cells are responsible for secreting glucagon when blood glucose levels are below normal. Glucagon encourages the liver to synthesise glucose from glycogen stores, thus preventing hypoglycaemia. The delta cells are responsible for secreting somatostatin which acts as an inhibitor for the insulin and glucagon released, thus preventing the detrimental effects that would arise from the uncontrolled secretion of these two hormones.

Figure 1:
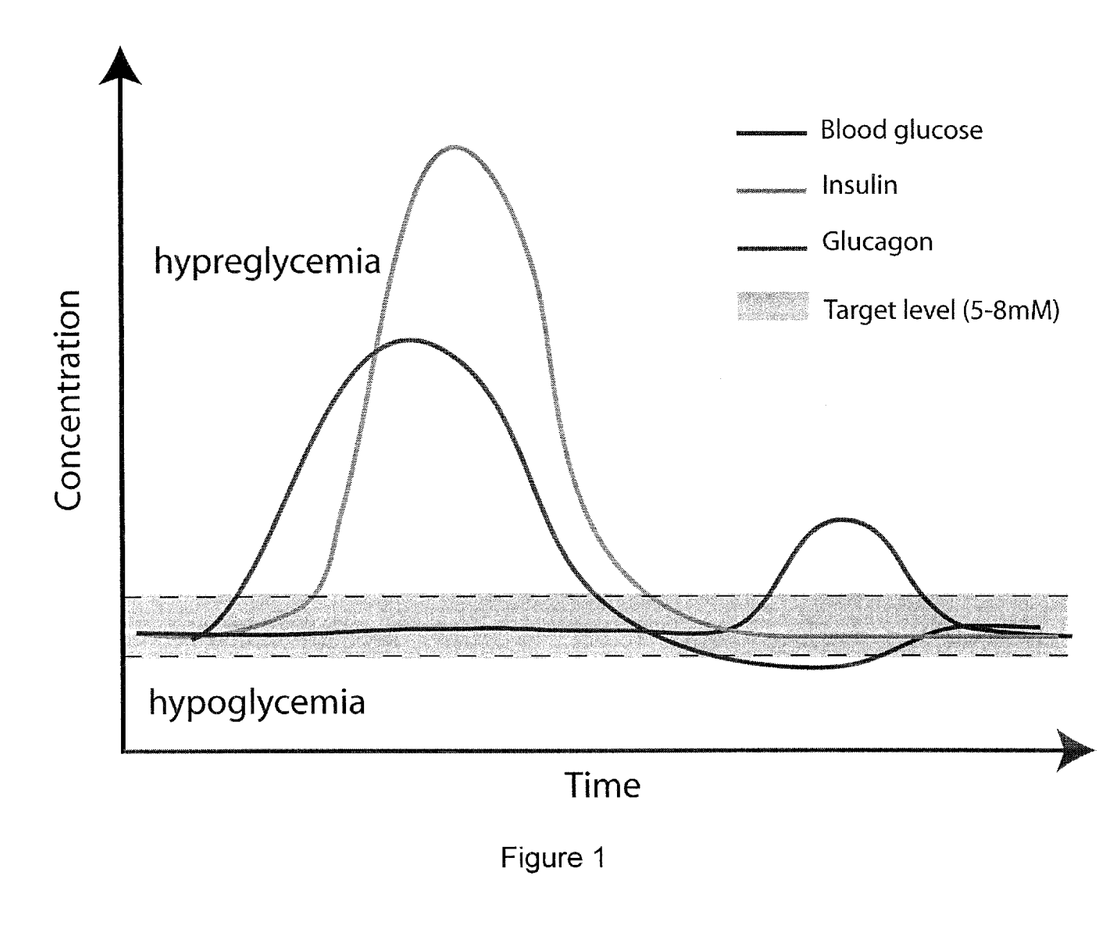
FIG. 1 illustrates a typical regulation profile of insulin and glucagon.

FIG. 1 illustrates a typical regulation profile of insulin and glucagon. When a meal is eaten and broken down into glucose, elevation of blood glucose occurs to levels of hyperglycaemia. This stimulates insulin release that causes peripheral tissue to uptake and consume glucose. In the event of too much insulin release, glucose levels undershoot below the nominal range to hypoglycaemia. Glucagon is then released which promotes glucose release from stores in the liver, bringing blood glucose levels back to there nominal range.

Diabetes mellitus, often referred to simply as diabetes, is a condition in which the body is unable to properly produce or use insulin to process the glucose (sugar) in the blood, resulting in abnormally high blood sugar levels. There are two main types of diabetes, Type I or Type II. Type I diabetes, also known as insulin-dependent diabetes, is an auto-immune disease which results in loss of the beta cells, leading to a deficiency of insulin. This occurs mainly during childhood and current treatment is by insulin injection before meals. Furthermore, in established Type I diabetes, there is a reduced glucagon response to hypoglycaemia that is partially (or perhaps wholly) attributable to the absence of paracrine insulin action. Type II diabetes, also known as non-insulin dependant diabetes, usually occurs at an older age and is due to an insulin resistance or reduced insulin sensitivity. This causes a need for abnormally high amounts of insulin and diabetes develops when the beta cells cannot meet this demand. Treatment usually consists of a carefully managed diet and medication. However, in extreme cases injections may be required. Without monitoring and treatment diabetes can lead to hyperglycaemia, which can in turn lead to blindness, renal failure, coma and eventually death.

Current regimes for treating Type I diabetes are mainly based on injections of subcutaneous insulin several times a day, in dosages determined by intermittent blood glucose measurements. The Diabetes Control and Complications Trial (DCCT) was a major clinical study conducted by the US National Institute of Diabetes and Digestive and Kidney Diseases. The results of this trial demonstrated that intensive management using these principles could reduce complications by up to 76% (see New England Journal of Medicine, 329(14), Sep. 30, 1993). However, this reduction in hyperglycaemia related complications was at the expense of hypoglycaemia, which occurs when blood glucose drops below normal levels, especially at levels of glycosylated haemoglobin (HbA1c) below 7.5%. If not controlled, hypoglycaemia can also cause coma and eventually death. In other studies, intensive management resulted in people still spending approximately 30% of the day with glucose values of more than 10 millimole per litre (mM), and more than two hours per day in hypoglycaemia.

A possible alternative method of treating diabetes involves the use of an artificial pancreas device. Such devices could potentially bring significant improvements in the treatment of the disease and the quality of life of diabetics. Principally an artificial pancreas is closed-loop system based on the function of the beta cells for controlling hyperglycaemia, requiring a glucose sensor to determine the blood sugar levels, a control algorithm to calculate the required insulin dose and an infusion pump to deliver insulin to the blood.

Artificial pancreas control algorithms are currently either based on Proportional-Integral Derivative (PID) control or Model-based Predictive Control (MPC). PID control is a generic feedback loop mechanism which has been widely adopted in industrial systems due to its simplicity and ease of tunability. PID algorithms attempt to correct the error between a measured value of a process variable and the desired value (or setpoint) by calculating and then outputting a corrective action that can adjust the process accordingly. When used in glucose homeostasis applications, PID algorithms can continually adjust insulin infusion rates by assessing the departure of measured glucose levels from a target glucose level (the proportional component), the area-under the curve between ambient and target glucose levels (the integral component) and the change in ambient glucose level (the derivative component) (see "Closed-loop insulin delivery—the path to physiological glucose control," Advanced Drug Delivery Reviews, vol. 56, no. 2, pp. 125-144, 2004). However, algorithms of this sort are not immune to patient variability and thus require individual tuning each time a new patient uses a device. In addition to this, the control is not pro-active, having a high associated risk of hypoglycaemia, and does not take into consideration constraints such as the bounds of hyperglycaemia and hypoglycaemia.

MPC is a control method which continually computes the optimal solution for insulin infusion for each sample of glucose taken (see "The intravenous route to blood glucose control," IEEE Engineering in Medicine and Biology Magazine, vol. 20, no. 1, pp. 65-73, 2001). It has the ability to estimate present and future insulin delivery rates and glucose behaviour. This is significant as the control can be pro-active instead of reactive, which is an important feature for patient safety. However, these methods involve the prediction of future values that require an accurate process model, and although the models currently used do capture the glucose-insulin behaviour to some degree, they do not account for patient variability over time which can lead to significant performance degradation. Whilst several approaches have been developed to adaptively change these internal models to fit the actual patient data, these approaches tend to be complex to design, with many parameters, and require high computational power to compute an optimisation for each time step.

A recent study (see "Continuous glucose monitoring and closed-loop systems," Diabetic Medicine, vol. 23, no. 1, pp. 1-12, 2006) has shown that patients using such artificial pancreas systems face a significant risk of experiencing hypoglycaemia. Furthermore, in the patients who did not experience hypoglycaemia, a postprandial increase in glucose of 3 mM or more was found, which kept the patient in hyperglycaemia.

SUMMARY

It is an object of the present invention to overcome or at least mitigate the problems noted above. In particular, it is an object of the present invention to control episodes of hypoglycaemia, and keep blood glucose at normal levels.

According to a first aspect of the present invention there is provided a controller for controlling a glucagon pump. The controller comprises an input for receiving an input signal indicative of a measured blood glucose concentration, an output for providing a pulsed glucagon pump drive signal, each pulse being arranged to cause a glucagon pump to deliver a volume of glucagon, and a processing unit for setting the pulse frequency of the pump drive signal in dependence upon the input signal, such that when the input signal indicates that the measured blood glucose concentration is above a threshold concentration the pulse frequency is zero, and when the input signal indicates that the measured blood glucose concentration is below the threshold concentration the pulse frequency is increased as the measured blood glucose concentration decreases.

The processing unit may be arranged to implement an integrate and fire model to simulate the electrical response of a pancreatic alpha cell to blood glucose concentration. Alternatively, the processing unit may be arranged to implement a Dirac delta function model to simulate the electrical response of a pancreatic alpha cell to blood glucose concentration. The processing unit may also be arranged to convert the simulated electrical response into the pulsed glucagon pump drive signal.

According to a second aspect of the present invention there is provided a system for controlling blood glucose concentration. The system comprises a glucagon pump controller according to the first aspect described above, and a glucagon pump. The system may further comprise an insulin pump controller and an insulin pump.

The system may also comprise an adjustment unit for accepting input of patient specific information and for using the patient specific information to modify the volume of glucagon delivered by the glucagon pump in response to each pulse of the pump drive signal.

According to a third aspect of the present invention there is provided a method of operating a controller for controlling a glucagon pump. The method comprises receiving an input signal indicative of a measured blood glucose concentration, processing the input signal to generate a pulsed glucagon pump drive signal, each pulse being arranged to cause a glucagon pump to deliver a volume of glucagon, setting the pulse frequency of the pump drive signal in dependence upon the input signal, such that when the input signal indicates that the measured blood glucose concentration is above a threshold concentration the pulse frequency is zero and when the input signal indicates that the measured blood glucose concentration is below the threshold concentration the pulse frequency is increased as the measured blood glucose concentration decreases, and outputting the pulsed glucagon pump drive signal.

DETAILED DESCRIPTION

For healthy regulation of blood glucose levels the irregularities experienced by patients using known artificial pancreas systems need to be avoided. In order to achieve this regulation, it is proposed here to make use of an artificial alpha cell to control episodes of hypoglycaemia, wherein the glucagon response of the artificial alpha cell more accurately replicates the biochemical response of a healthy pancreatic alpha cell. In doing so, this bio-inspired artificial alpha cell provides that the amount of glucagon delivered in order to control an episode of hypoglycaemia will also more accurately replicate that secreted by a healthy pancreatic alpha cell. This bio-inspired behaviour differs from known algorithms used to control glucose excursions, which do so without regard for how much of the hormone is delivered.

The glucagon released from pancreatic alpha cells is a direct consequence of the electrophysiological mechanisms which occur within the cell. Inside a pancreatic alpha cell the cytoplasm (cellular material) contains various ions, which can flow in and out of the cell through the cell membrane via gated ion channels. Different concentrations of these ions inside the cell and in the extra-cellular fluid in which the cell rests cause a potential difference across the cell membrane. Glucose transporter molecules transfer glucose across the membrane into the alpha cell, and once inside this glucose is then broken down into products that cause activity of the ion channels, thus changing the potential difference of the cell membrane. If the glucose concentration falls below a threshold then the resulting change in the potential difference across the membrane generates action potentials, and it is this electrical activity that triggers glucagon secretion from the alpha cell. In addition, it has been shown that the frequency at which these action potentials occur increases as the glucose concentration decreases. For example, "Tight coupling between electrical activity and exocytosis in mouse glucagon-secreting alpha-cells", Diabetes, vol. 49, iss. 9 pp. 1500-1510, 2000, illustrates the membrane potential of an alpha cell in response to a step change in glucose concentration from 3 mM to 20 mM.

Figure 2:
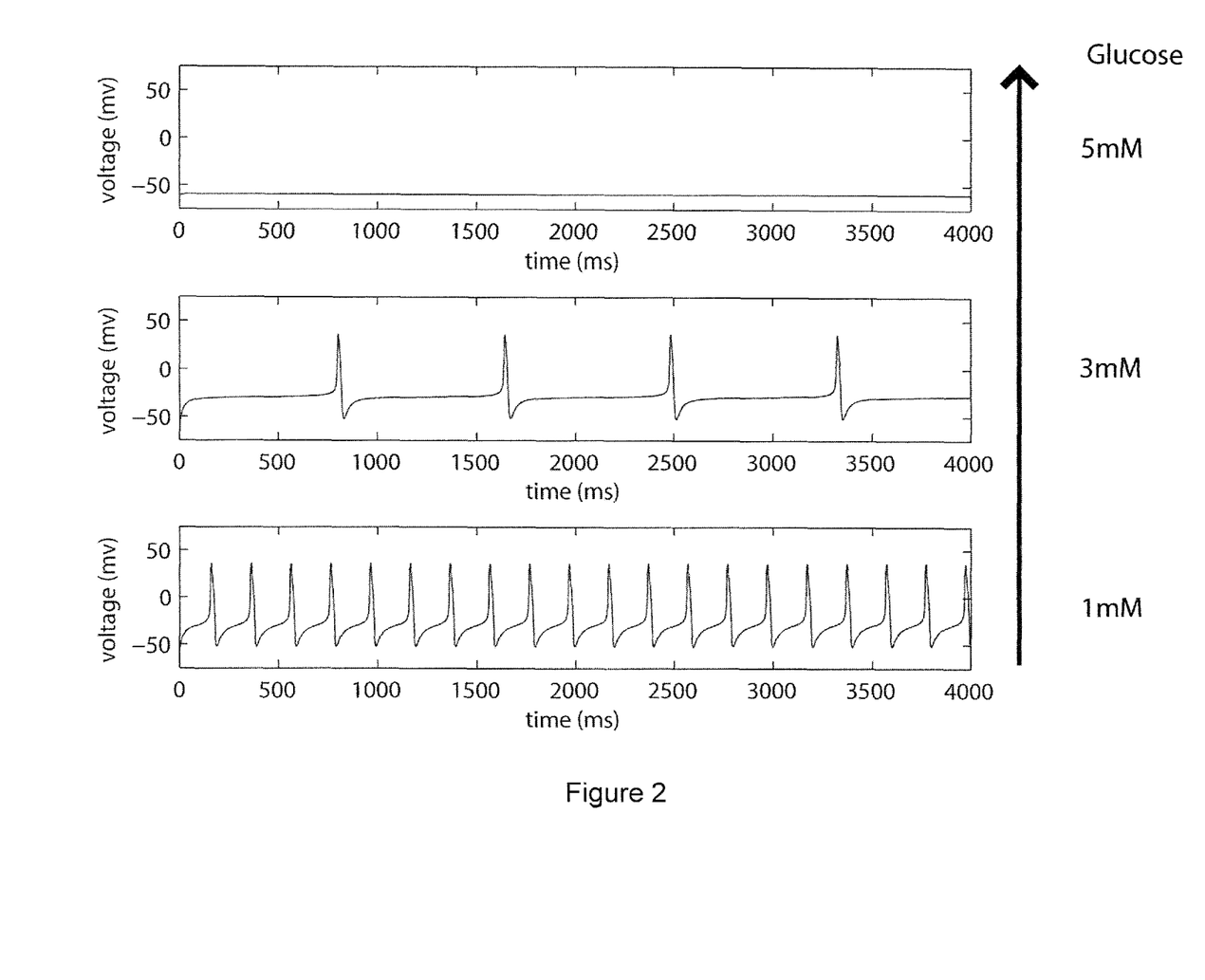
FIG. 2 illustrates an example of the output of an artificial alpha cell for increasing glucose concentrations.

The bio-inspired artificial alpha cell replicates this behaviour by making use of an input signal indicative of a measured blood glucose concentration to derive a pulsed or spiked signal for driving a glucagon pump. The frequency of pulses or spikes in this pump drive signal is set in dependence upon the input signal. When the input signal indicates that the measured blood glucose concentration is above a threshold concentration then the pulse frequency is zero. When the input signal indicates that the measured blood glucose concentration is below the threshold concentration (i.e. at hypoglycaemic levels), then the pulse frequency is increased as the measured blood glucose concentration decreases. FIG. 2 illustrates an example of the output of a bio-inspired artificial alpha cell for increasing glucose concentrations. Each pulse of this output drives the glucagon pump to deliver a predefine volume or bolus of glucagon.

This behaviour may be described mathematically using a Dirac delta function where $V_{mem}$ is the membrane potential and G is the glucose concentration:

$$V_{mem} = 0, G > 5 \text{ mM} \qquad \text{Equation 1}$$

$$V_{mem} = \sum_{n=1}^{\infty} A \times \delta(t - nT_n) \text{ for } G < 5 \text{ mM} \qquad \text{Equation 2}$$

$$\text{where } T_n = \alpha \times G_n \times 1000 \qquad \text{Equation 3}$$

Equation 2 gives the membrane potential for glucose concentrations below 5 mM where, in a time window t, the membrane potential consists of n spikes of amplitude A repeating every $T_n$. $T_n$ is dependant on the instantaneous glucose concentration $G_n$ and is given by Equation 3, such that a decrease in the instantaneous glucose concentration $G_n$ decreases the time delay $T_n$ between each spike, thereby increasing the frequency at which the spikes occur. $\alpha$ is an adjustable parameter that can be used to calibrate the spike period $T_n$ in dependence upon glucose concentration $G_n$.

Figure 3:
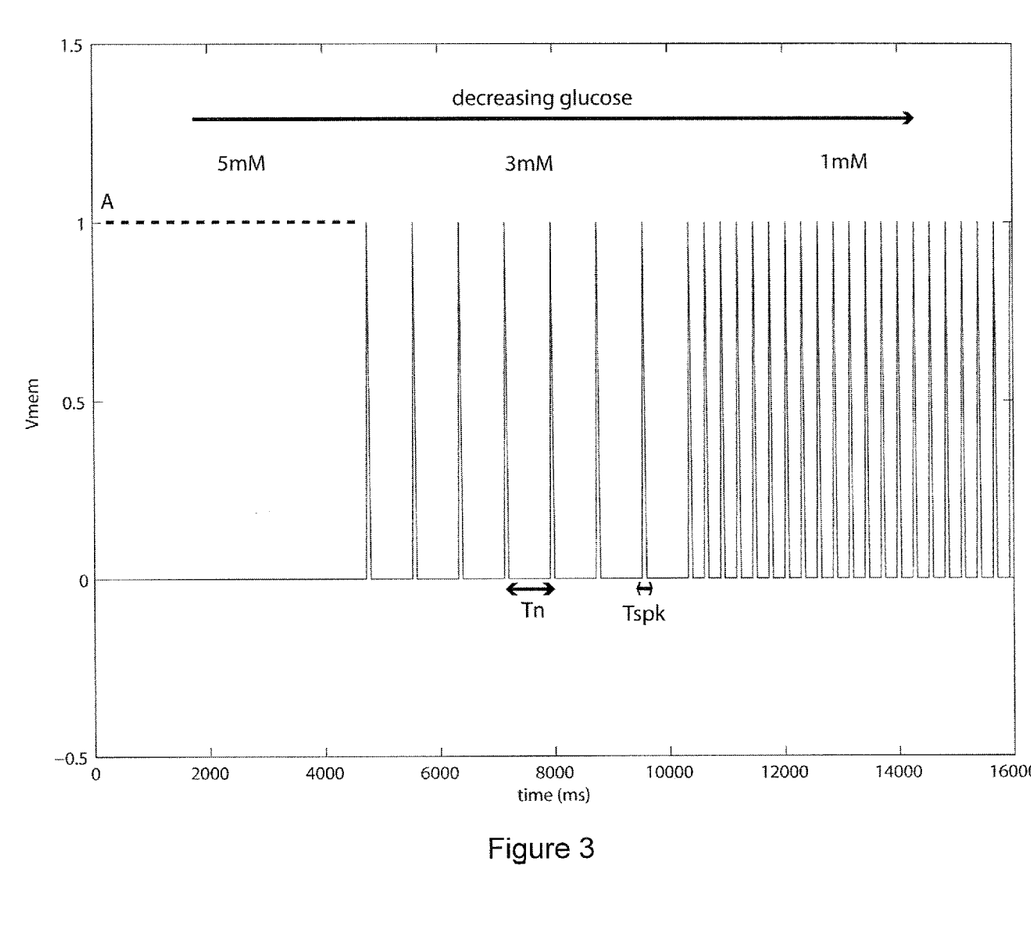
FIG. 3 illustrates an example of the output of a microcontroller or PC-based controller for decreasing values of glucose concentration.

This mathematical description of the behaviour of a pancreatic alpha cell can be implemented using either hardware or software in order to control a glucagon pump, thereby providing an artificial alpha cell device that replicates the response of a biological alpha cell. FIG. 3 illustrates an example of the output of a microcontroller or PC-based controller implementing this mathematical model for decreasing values of glucose concentration, where $T_{spk}$ is the duration of the spike.

The behaviour of the alpha cell can also be represented using an integrate and fire model. In this model the alpha cell is represented in time by:

$$C_{mem} \frac{dV_{mem}}{dt} = I(t) \qquad \text{Equation 4}$$

Equation 4 is the time derivative of the law of capacitance (Q=CV) where $C_{mem}$ is the capacitance of the cell membrane as determined by the concentration of charged ions on either side of the membrane. When an input current is applied, the membrane voltage $V_{mem}$ increases with time until it reaches a constant threshold $V_{th}$, at which point a delta function spike occurs and the voltage is reset to its resting potential, after which the model continues to run. The firing frequency of the model thus increases linearly as input current increases. A "leak" term should be added to the membrane potential, reflecting the diffusion of ions that occurs through the membrane when some equilibrium is not reached in the cell. Modifying Equation 4 to take account of this leak current gives:

$$C_{mem} \frac{dV_{mem}}{dt} = I(t) - I_{leak} \qquad \text{Equation 5}$$

Figure 4:
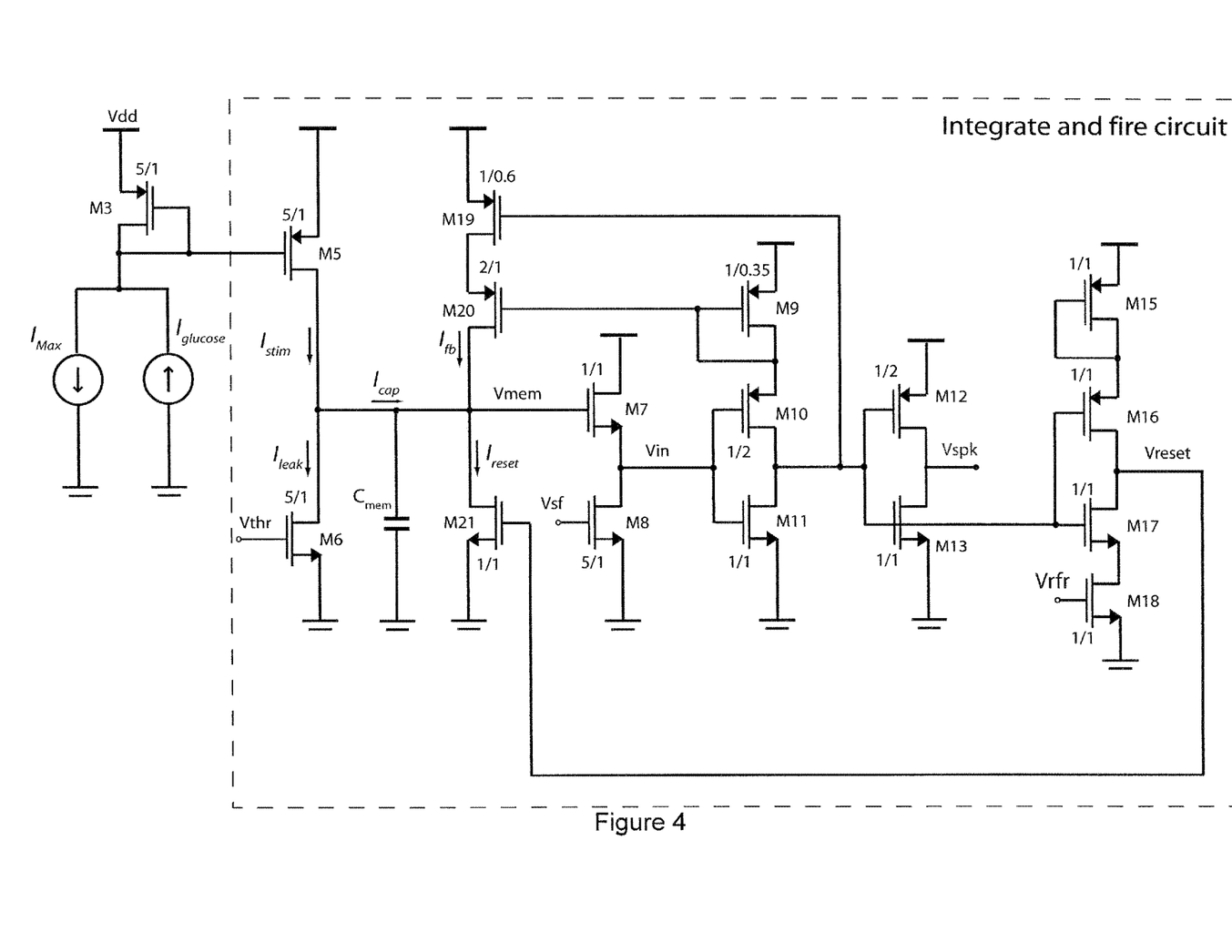
FIG. 4 illustrates an example of an integrate and fire circuit suitable for implementing an artificial alpha cell.

FIG. 4 illustrates an example of a circuit suitable for implementing an integrate and fire model of an alpha cell. This is a complementary metal-oxide semiconductor (CMOS) based circuit, which uses a combination of p-type and n-type metal-oxide-semiconductor field-effect transistors (MOSFETs). Such a circuit can approximate action potentials and thus waveforms of the type seen in alpha cells by integrating currents representing glucose concentration on a capacitor, and resetting when a threshold is reached. Using this circuit Equation 5 becomes $$C_{mem} \frac{dV_{mem}}{dt} = I_{stim} - I_{leak} \qquad \text{Equation 6}$$

$$\text{where and } I_{stim} = I_{max} - I_{glucose} \qquad \text{Equation 7}$$

$I_{glucose}$ is the input from a glucose sensor and $I_{max}$ is set to the maximum current from the glucose sensor such that the circuit stimulation current $I_{stim}$ has an inverse relationship with $I_{glucose}$, thereby implementing the inverse glucagon response of the alpha cell to glucose concentration. From Equation 6 it can be seen that the capacitor, $C_{mem}$, will only start charging when the stimulation current exceeds the leakage current, leading to a rise in the membrane voltage $V_{mem}$.

As the capacitor charges and $V_{mem}$ rises above a threshold set by $V_{sf}$, using the source follower M7-M8 in FIG. 4, the voltage $V_{in}$ will begin to rise according to:

$$V_{in} = k(V_{mem} V_{sf}) \qquad \text{Equation 8}$$

where k is the sub-threshold slope coefficient. Once $V_{in}$ approaches the switching threshold of the inverter M10-M11, the feedback current, $I_{fb}$, begins to increase, adding positive feedback and making $V_{in}$ rise faster and causing the inverter to switch instantaneously. In doing so it reduces the time that both M10-M11 are on and reduces power.

When $V_{in}$ is high this sets the reset voltage $V_{reset}$ high, turning on the bleed transistor M21 which instantaneously discharges the membrane capacitance $C_{mem}$ and produces a spike at $V_{spk}$. The membrane capacitance $C_{mem}$ can only begin to charge again once the reset voltage $V_{reset}$ goes low by discharging through the channel resistance of transistor M18. This resistance can be tuned using the voltage $V_{rfr}$ which sets the refractory period of the cell (e.g. the interval during which a second action potential cannot be initiated) and ultimately the maximum spiking frequency.

As such, when $I_{stim}$ exceeds a threshold, the dependence of the spike frequency on the stimulation current can be approximated as:

$$f_{spike} \approx \frac{I_{cap} \cdot f_{rfr}}{I_{cap} + C_{mem} \cdot V_0 \cdot f_{rfr}} \qquad \text{Equation 9}$$

$$\text{where } I_{cap} = I_{stim} - I_{leak} \qquad \text{Equation 10}$$

$f_{rfr}$ is the maximum spiking frequency of the cell, given by $f_{rfr}=1/t_{rfr}$, where $t_{rfr}$ is the refractory period of the cell, and $V_o$ is the threshold voltage of the inverter M10-M11.

Glucose concentrations below around 5 mM should cause the integrate and fire circuit of FIG. 4 to spike. Therefore, given an $I_{glucose}$ mapping of 1 nA to 5 nA for glucose concentrations of 1 mM to 5 mM, and an $I_{max}$ of 5 nA, $I_{stim}$ will vary from 5 na to 1 na for glucose concentrations of 1 mM to 5 mM. For such currents it can be assumed that:

$$I_{cap} << C_{mem} \cdot V_0 \cdot f_{rfr} \quad \text{Equation 11}$$

and therefore the spike or pulse period, $T_n$, can be given by:

$$T_n = \frac{C_{mem} \cdot V_0}{I_{max} - I_{glucose} - I_{leak}} \quad \text{Equation 12}$$

Figure 5:
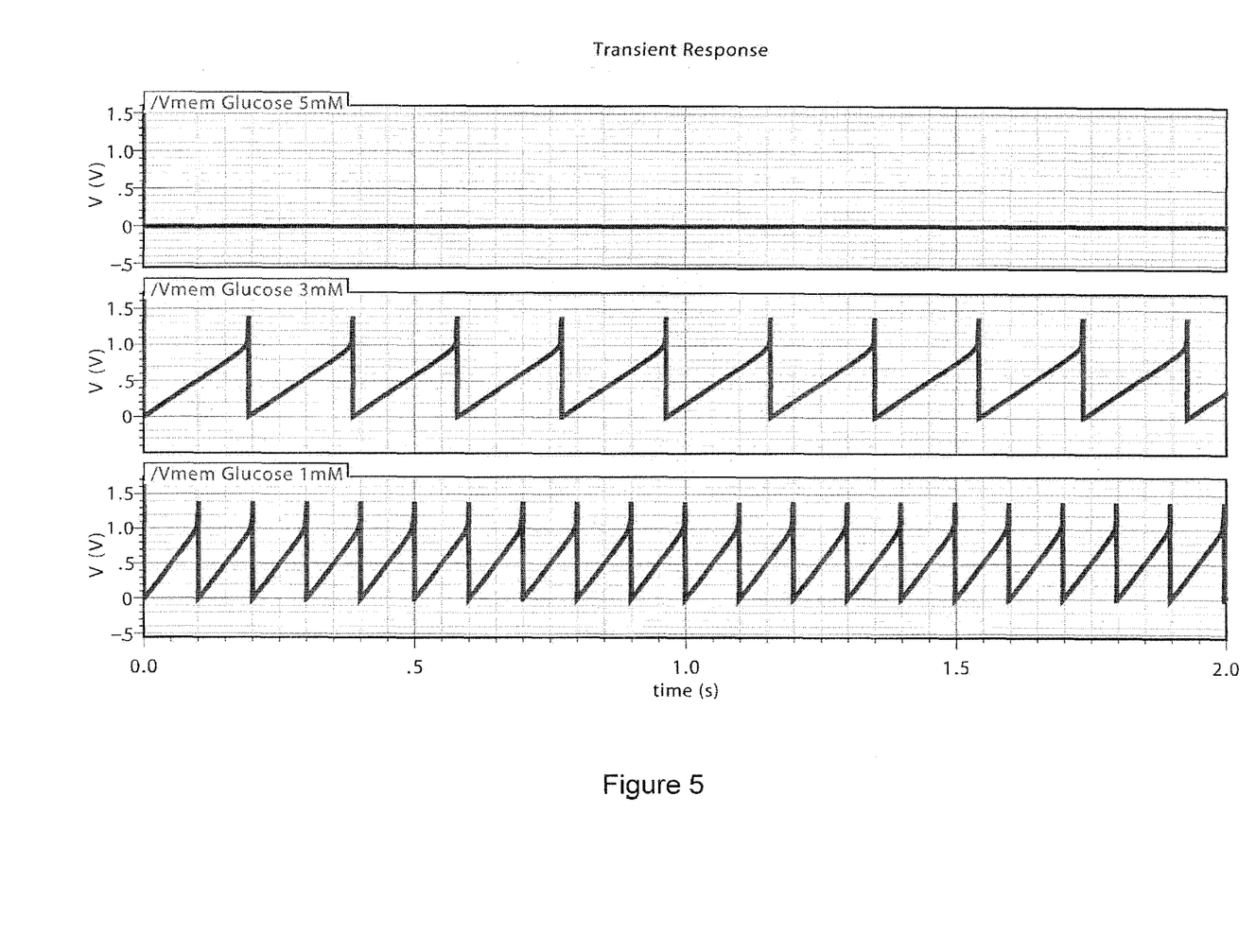
FIG. 5 illustrates an example of the output of an integrate and fire circuit for decreasing values of glucose concentration.

From Equation 12 it can be seen that, as in the alpha cell, the spike period is inversely proportional to the glucose concentration, represented by $I_{glucose}$, and may be defined by the magnitude of the membrane capacitance, $C_{mem}$. As such, $C_{mem}$, $I_{max}$, $I_{glucose}$ and $I_{leak}$ can be defined or tuned to give the spike period required for a particular individual. FIG. 5 illustrates an example of the output of an integrate and fire circuit, as described above, for decreasing values of glucose concentration.

The output of such an artificial alpha cell is then used to control a glucagon pump thereby replicating the glucagon response of a healthy pancreatic alpha cell to blood glucose concentration. If required, a comparator circuit can also be used to convert the spiked or pulsed output of the artificial alpha cell into pulses that are suitable for driving the glucagon pump, such that in response to each pulse the glucagon pump will deliver a set volume of glucagon. In addition, as well as tuning the frequency of the pulses to a particular individual, the volume of glucagon delivered can be varied by some patient specific weighting. This weighting may take into account a number of factors, such as the patient's tolerance to glucagon, and can be a function of a number of variables, such as the glucose, insulin, ketone and fatty acid concentrations in the patient's blood.

Figure 6:
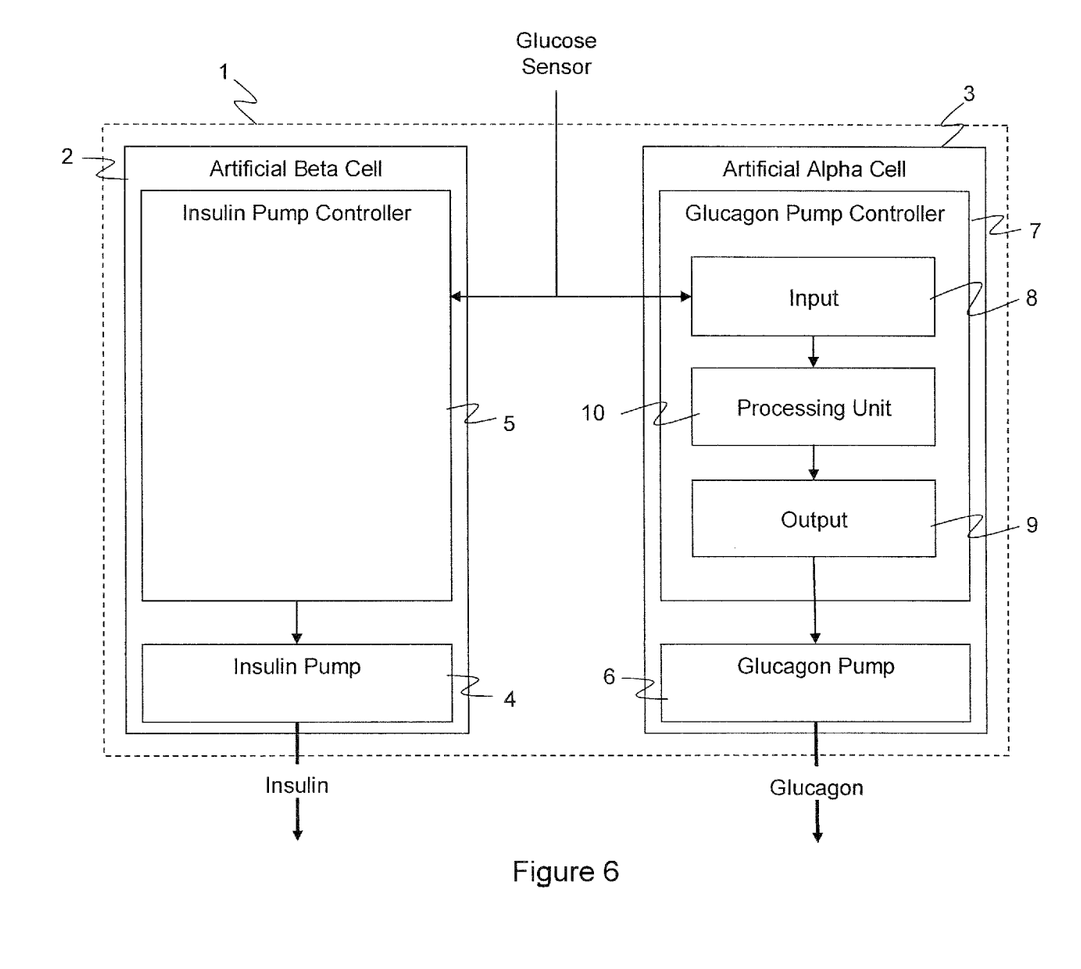
FIG. 6 illustrates schematically a system for controlling blood glucose concentration.

Furthermore, the artificial alpha cell can be combined with those known devices for controlling hyperglycaemia, thereby providing a system for preventing both hypoglycaemia and hyperglycaemia. FIG. 6 illustrates a schematic of such a system 1 for controlling blood glucose concentration. The system 1 comprises an artificial beta cell 2, and an artificial alpha cell 3. The artificial beta cell 2 comprises an insulin pump 4 and an insulin pump controller 5 of the prior art.

The artificial alpha cell 3 comprises a glucagon pump 6 and a glucagon pump controller 7. The glucagon pump controller 7 can be implemented as a combination of hardware and/or software. The glucagon pump controller 7 comprises an input 8 for receiving an input signal indicative of a measured blood glucose concentration, an output 9 for providing a pulsed glucagon pump drive signal, each pulse being arranged to cause a glucagon pump to deliver a volume of glucagon, and a processing unit 10 for setting the pulse frequency of the pump drive signal in dependence upon the input signal. When the input signal indicates that the measured blood glucose concentration is below a threshold concentration, the processing unit 10 increases the pulse frequency when the measured blood glucose concentration decreases and, conversely, decreases the pulse frequency when the measured blood glucose concentration increases. When the input signal indicates that the measured blood glucose concentration is above the threshold concentration, the processing unit 10 sets the pulse frequency to zero.

It will be appreciated by the person of skill in the art that various modifications may be made to the above-described embodiments without departing from the scope of the present invention.

What is claimed is:

1. A controller for controlling a glucagon pump, the controller comprising:
    an input arranged to receive an input signal indicative of a measured blood glucose concentration;
    an output arranged to provide a pulsed glucagon pump drive signal, each pulse being arranged to cause a glucagon pump to deliver a volume of glucagon; and
    a processing unit arranged to set a pulse frequency of the pump drive signal in dependence upon the input signal, such that when the input signal indicates that the measured blood glucose concentration is above a threshold concentration the pulse frequency is zero and when the input signal indicates that the measured blood glucose concentration is below the threshold concentration the pulse frequency is increased as the measured blood glucose concentration decreases, wherein the processing unit comprises a CMOS based circuit arranged to implement an integrate and fire model to simulate the electrical response of a pancreatic alpha cell to blood glucose concentration, the CMOS based circuit comprising metal-oxide-semiconductor field-effect transistors (MOSFETs),
    wherein the CMOS based circuit is conductively coupled to said input, said input being conductively coupled to an output of a glucose sensor and arranged to receive an output current from the glucose sensor, and further arranged to generate action potentials approximating action potentials of alpha cells and wherein said action potentials determine said pulsed glucagon pump drive signal.

2. The controller as claimed in claim 1, wherein the processing unit is arranged to convert a simulated electrical response of a pancreatic alpha cell to blood glucose concentration into the pulsed glucagon pump drive signal.

3. A system for controlling blood glucose concentration, the system comprising:
    a glucagon pump controller according to claim 1; and
    a glucagon pump.

4. The system as claimed in claim 3, and further comprising:
    an insulin pump controller; and
    an insulin pump.

5. The system as claimed in claim 3, and further comprising an adjustment unit for accepting input of patient specific information and for using the patient specific information to modify the volume of glucagon delivered by the glucagon pump in response to each pulse of the pump drive signal.

6. A method of operating a controller for controlling a glucagon pump, the method comprising:
    receiving an input signal indicative of a measured blood glucose concentration;
    processing the input signal to generate a pulsed glucagon pump drive signal, each pulse being arranged to cause a glucagon pump to deliver a volume of glucagon, setting the pulse frequency of the pump drive signal in dependence upon the input signal, such that when the input signal indicates that the measured blood glucose concentration is above a threshold concentration the pulse frequency is zero and when the input signal indicates that the measured blood glucose concentration is below the threshold concentration the pulse frequency is increased as the measured blood glucose concentration decreases, wherein the pulsed glucagon pump drive signal is generated by a processing unit comprising a CMOS based circuit arranged to implement an integrate and fire model to simulate the electrical response of a pancreatic alpha cell to blood glucose concentration, the CMOS based circuit comprising metal-oxide-semiconductor field-effect transistors (MOSFETs) and wherein the CMOS based circuit generates action potentials approximating action potentials of alpha cells and wherein said action potentials determine said pulsed glucagon pump drive signal; and outputting the pulsed glucagon pump drive signal.

* * * * *